United States Patent [19]

Klagsbrun

[11] 4,440,860

[45] Apr. 3, 1984

[54] STIMULATING CELL GROWTH

[75] Inventor: Michael Klagsbrun, Newton, Mass.

[73] Assignee: The Children's Medical Center Corporation, Boston, Mass.

[21] Appl. No.: 239,523

[22] Filed: Mar. 2, 1981

Related U.S. Application Data

[63] Continuation-in-part of Ser. No. 113,229, Jan. 18, 1980, abandoned, which is a continuation-in-part of Ser. No. 953,491, Oct. 23, 1978, abandoned.

[51] Int. Cl.$^3$ .......................... C12N 5/00; C12N 5/02; C12M 3/00; C12M 3/04
[52] U.S. Cl. ..................................... 435/240; 435/241; 435/284; 435/285; 435/286
[58] Field of Search ............... 435/240, 241, 284, 285, 435/286

[56] References Cited

U.S. PATENT DOCUMENTS

| | | | |
|---|---|---|---|
| 3,644,326 | 2/1972 | Pien | 260/112 R X |
| 3,664,925 | 5/1972 | Sonenberg et al. | 260/112 R X |
| 4,018,752 | 4/1977 | Buhler et al. | 260/112 R |
| 4,042,576 | 8/1977 | Eustache | 260/112 R |
| 4,066,405 | 1/1978 | Henkin | 260/112 R X |
| 4,107,014 | 8/1978 | Suzuki et al. | 260/112 R X |

OTHER PUBLICATIONS

Journal of Cell Physiology, vol. 109, No. 2, pp. 223–234; 1981.
George H. Rothblat et al. editors, Growth, Nutrition and Metabolism of Cells in Culture, vol. II, p. 379; 1972.
Jakoby et al., editors, Methods in Enzymology, vol. LVIII Academic Press, p. 267; 1979.
Maciaz et al., "Hormonal Requirements of Baby Hamster Kidney Cells in Culture", Cell Biology International Reports, Jan. 1980.
Groves (1965), Biochem. Biophys. Acta. 100, 154–162.
Querinjean et al. (1971), Eur. J. Biochem. 20, 420–425.
Butler et al., *In Lactation*, Larson et al. ed., pp. 217–255, (Academic Press, New York, 1974).
Hayashi et al. (1976) *Nature* 259, 132–134.
Hutchings et al. (1978), *Proc. Nat'l. Acad. Sci.* U.S.A. 75, 901–904.
Rizzino et al. (1978), *Proc. Nat'l. Acad. Sci.* U.S.A. 75, 1844–1848.
Mather et al., *Proceedings of the International Workshop for Cell, Tissure and Organ Cultures in Neurobiology*, Federoff, ed., pp. 619–630, (Academic Press, New York 1978).
Pena et al. "Fibroblast to Substratum Contacts Mediated by the Different Forms of Fibronectin", *Cell Biology International Reports*, vol. 2, No. 4, 1978.
Grinnel et al. (May 1979), Initial Adhesion of Human Fibroblasts in Serum-Free Medium: Possible Role of Secreted Fibronectin, *Cell.*, vol. 17, 117–120.

*Primary Examiner*—Robert J. Warden

[57] ABSTRACT

Compositions and methods for promoting cell growth featuring, in one aspect, cell culture media containing milk or colostrum and fibronectin; fibronectin is preferably pre-coated onto the culture substrate.

33 Claims, 9 Drawing Figures

STIMULATING CELL GROWTH

BACKGROUND OF THE INVENTION

This application is a continuation-in-part of Klagsbrun, "Stimulating Cell Growth," Ser. No. 113,229, filed Jan. 18, 1980, which in turn is a continuation-in-part of Klagsbrun, "Stimulating Cell Growth," Ser. No. 953,491, filed Oct. 23, 1978 both now abandoned.

This invention relates to cell growth and proliferation.

It is known that mammalian serum contains an ingredient ("factor") capable of inducing growth of cells in culture; bovine serum is widely used for that purpose. The growth factor in human serum has been isolated and found to be a protein having a molecular weight of about 13,000 and an isoelectric point of about 9.7. Growth factors have also been found in the pituitary gland, in the submaxillary gland, in brain and in cartilage.

Groves (1965) Biochem. Biophys. Acta. 100, 154–162 has reported the presence of the blood iron-binding protein transferrin in milk.

Querinjean et al. (1971) Eur. J. Biochem. 20: 420–425 have found that lactoferrin, an iron-binding protein similar to transferrin, is present in milk.

Butler et al. in *In Lactation,* Larson et al. ed., pp. 217–255 (Academic Press, New York 1974) have found that the lactoferrin level of colostrum declines rapidly during the postpartum period.

Five articles report that several cell types can grow in serum-free media which contain various mixtures of hormones, mitogens and other factors including, in all the mixtures, transferrin: Hayashi et al. (1976) Nature 259, 132–134; Hutchings et al. (1978) Proc. Natl. Acad. Sci. U.S.A. 75, 901–904; Mather et al. in *Proceedings of the International Workshop for Cell, Tissue and Organ Cultures in Neurobiology,* Federoff, ed. pp. 619–630 (Academic Press, New York 1978); Taub et al. (in press) Proc. Nat'l. Acad. Sci. U.S.A.; Rizzino et al. (1978) Proc. Nat'l. Acad Sci. U.S.A. 75, 1844–1848.

A problem encountered in the culture of some cell types, e.g., uncloned epithelial cells, is fibroblast overgrowth. An approach to the problem has been the use of selective media which inhibit fibroblast growth.

SUMMARY OF THE INVENTION

We have discovered a potent, new growth factor, with 50–100 times greater specific activity than even that in serum. The invention thus features, in one aspect, a concentrate of this growth factor, which is a protein derived from mammalian (e.g., human, bovine, sheep) milk obtained less than about 56 hours post-partum (hereinafter "colostrum"), and the method of concentrating it based on its physical properties, which include a molecular weight below about 20,000 (at least for human and bovine colostrum) and an isoelectric point of between about 4.4 and 4.8.

In preferred embodiments human or bovine colostrum is collected a short time after birth, fat and inactive protein are removed, and gel filtration, isoelectric focussing and preparative polyacrylamide gel electrophoresis are carried out. The concentrate is useful in cell growth media for tissue culture, and, e.g., as a food additive for humans and other animals.

We have also found that defatted colostrum which has not been further purified is useful in cell growth media for tissue culture of certain cell types, e.g., kidney, gastrointestinal, and bile duct epithelial cells, and myoblasts. We have also found that colostrum added to conventional serum-based media provides a new medium which is more effective in promoting cell proliferation than either serum or colostrum alone and has the added advantage of being cheaper than conventional serum-based media.

We have found that some cell types, e.g., primary and early passage fibroblasts (fibroblasts which have been transferred to fresh medium fewer than about 12 times following removal from an animal) and normal rat embryo cells, unlike epithelial cells, fail to proliferate in colostrum-containing media. This finding provides the basis for a further aspect of the invention, the use of colostrum in tissue culture media to prevent fibroblast overgrowth while promoting the proliferation of a desired cell type.

We have also discovered that, although milk which is not colostrum (hereinafter "milk") by itself fails to stimulate significant proliferation in normal cells, the addition of the iron-binding protein transferrin (T) to milk results in media which very effectively stimulate such proliferation. The invention thus features, in another aspect, inexpensive (compared to serum-based media) cell culture media containing either milk or colostrum, and transferrin. One or more of the additives insulin (I), epidermal growth factor (EGF) and fibroblast growth factor (FGF) can also be added to the media to further stimulate cell proliferation.

We have also discovered that an additional factor, the serum protein fibronectin, also enables milk-based media to support the proliferation of cultured cells, and also enhances the ability of colostrum to support cultured cell growth. An additional aspect of the invention therefore provides cell culture media containing colostrum or milk plus fibronectin, as well as, for some cell types, transferrin, insulin, epidermal growth factor, and fibroblast growth factor. In preferred embodiments, the fibronectin is coated onto the cell culture substrate (e.g., plate or dish) prior to plating the cells.

The finding that colostrum does not promote the proliferation of some cell types, and our discoveries that milk, in the absence of fibronectin or transferrin, does not promote proliferation of any cell types, and that both colostrum and milk do promote proliferation in malignant (cancerous and transformed) cells, provide the foundation for an additional aspect of the invention, a method of measuring the concentration of malignant cells in a sample. Colostrum or milk is added to nutrient medium which by itself does not kill or stimulate proliferation in eukaryotic cells. Cells from the sample are introduced into or onto the medium and the rate of cell proliferation is determined. Because practically the only cells which can grow in the milk-based medium are malignant cells, the proliferation rate is directly proportional to the concentration of malignant cells in the sample.

Other advantages and features of the invention will appear from the following description of preferred embodiments thereof, including the drawings.

DESCRIPTION OF PREFERRED EMBODIMENTS

Growth Factor Purification

Growth factor concentrate is obtained from colostrum by the following preferred process.

Fat is first removed, e.g., by centrifugation, by delipidization with alcohol-ether or alcohol-acetone, or by chloroform extraction.

Inactive proteins are then grossly removed, e.g., by contacting the colostrum with acetic acid, pH 4.3, for 2 hours and the removing the precipitate by centrifugation.

Isoelectric focusing and gel filtration are then carried out, in either order, to concentrate growth promoting protein.

Figure 1:
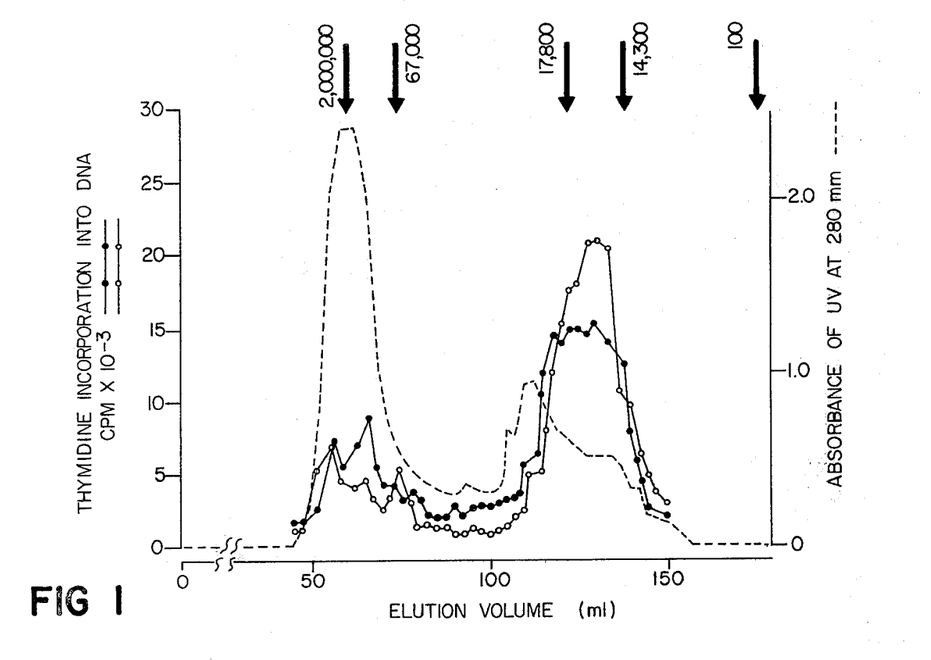
FIG. 1 is a gel filtration graph in which elution volume is measured on the horizontal axis; molecular weights for specific calibration markers are indicated along the top. On one vertical axis there is measured counts per minute $\times 10^{-3}$ for thymidine incorporation into DNA (a standard measure of DNA synthesis activity) for Balb/c 3T3 target cells (open connected dots) and human skin fibroblast target cells (solid connected dots). On the other vertical axis there is measured (dashed line) absorbance of UV light of 280 nm wavelength, giving a measure of the total protein content in each fraction.

FIG. 1 shows that in human colostrum the growth factor has a molecular weight between 14,300 and 17,800. However, it is possible that in the work leading to FIG. 1 a multimer form of the protein was measured, so that the basic protein unit could have a molecular weight ½ or even ¼ as large. Since the inactive protein in milk is mostly of molecular weight well above that of the growth factor (as shown by the dashed line in FIG. 1, measuring the total protein content in each fraction), a safe dividing line for molecular weight is about 20,000 for both human and bovine colostrum. Purification based on molecular weight is carried out with a 1.5 $\times$ 94 cm gel filtration column equilibrated with 0.055 M NaCl and 0.001 M $KH_2PO_4$, pH 7.0, and calibrated with proteins of known molecular weight. The sample is applied to the column and eluted with buffer at a flow rate of 11 ml/hr.

Figure 2:
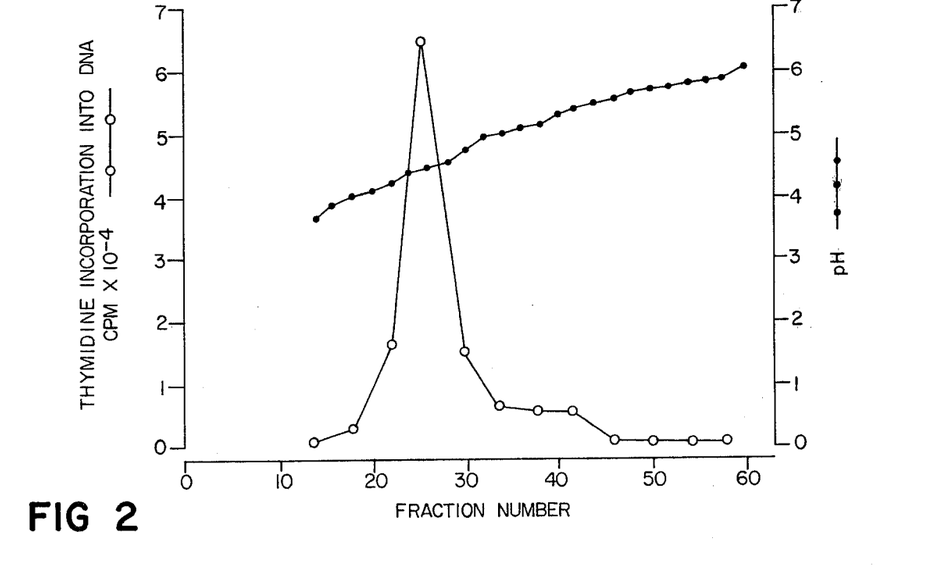
FIG. 2 is an isolectric focussing graph in which fraction numbers are measured on the horizontal axis. On one vertical axis there is measured (solid line connecting open dots) counts per minute $\times 10^{-4}$ for thymidine incorporation into DNA for Balb/c 3T3 target cells. On the other vertical axis is measured (dashed line) the corresponding pH for each fraction.

FIG. 2 shows that the growth factor in human colostrum has an isoelectric point between 4.42 and 4.68; this range is identical to the range we obtained for bovine colostrum. Purification based on isoelectric point is carried out with a vertical electrofocussing column with a capacity of 110 ml. The partially purified colostrum is dialyzed against distilled water, lyophilized, and introduced into 50% sucrose. A linear gradient of the sucrose is then formed (5-50% wt./vol.) and carrier ampholytes, at pH 4-6, are distributed in the gradient. The anode is placed in the lower electrode solution, which contains 0.16 M $H_3PO_4$ (pH 1.2)) and the cathode is placed in the upper electrode solution, which contains 0.25 M NaOH (pH 11.6). Isoelectric focusing is carried out at a constant voltage of 1650 V for 23 hr. at 4° C. In the case of human colostrum, the fraction having an isoelectric point between 4.4 and 4.8 (a range slightly wider, to provide a margin for error, than the 4.42 and 4.68 range) is collected.

The growth promoting concentrate can be further purified by preparative polyacrylamide gel electrophoresis, e.g., using the standard gel system of Ornstein and Davis.

The final concentrate, preferably in dry powder form, is particularly useful for tissue culture work, as its chemical makeup (unlike that of serum, e.g.) is known.

The amount of concentrate used will vary, depending on such factors as purity and cell type. Useful concentrations ordinary range between 1 ng and 5 g of concentrate per ml of medium.

Another possible use for the concentrate is as a food additive, e.g., in baby feeding formulas for humans and livestock.

Use of Colostrum in Growth Media

Bovine colostrum obtained eight hours after the birth of a calf is centrifuged at 12,000 g for 30 minutes to remove fat and cellular debris, diluted in Dulbecco's modified Eagles Medium (DMEM) to a concentration of 10 percent (v/v) or less, and sterilized by filtration. Diluted colostrum is used to supplement DMEM which contains 4.5 g of glucose per liter, 50 U of penicillin per ml and 50 mg of streptomycin per ml.

Figure 3:
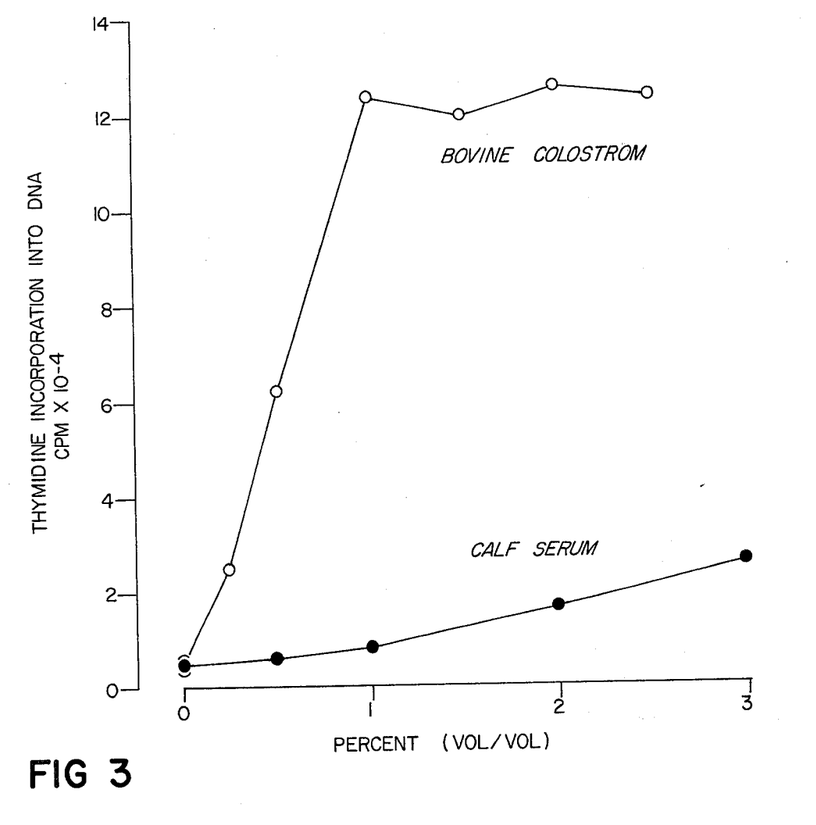
FIG. 3 is a graph of counts per minute $\times 10^{-4}$ for thymidine incorporation into DNA, against concentration (in volumetric percent) of bovine colostrum and calf serum, showing the greater specific activity of the colostrum.

The graph of FIG. 3 shows that bovine colostrum stimulates far greater mitogenic activity in BALB/c 3T3 cells than equal concentrations of bovine serum.

Figure 4:
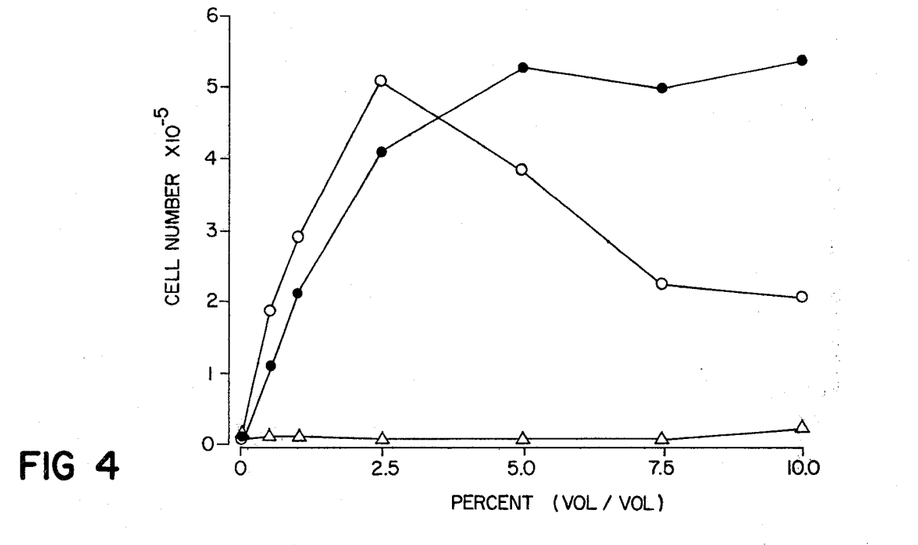
FIG. 4 is a graph of numbers of canine kidney epithelial (MDCK) cells counted after 12 days against concentration of: colostrum obtained 8 hours after birth of a calf (day 1 colostrum) (o); milk obtained 176 hours after the birth of the same calf (day 8 milk) ($\Delta$); and calf serum (.).

There is shown in FIG. 4 a dose response curve of MDCK cell proliferation in colostrum, milk and serum. Canine kidney epithelial cells (MDCK) in DMEM are seeded sparsely ($10^4$ cells/well, $5 \times 10^3$ cells/cm$^2$) into 24-well microliter plates. Six hours after plating the DMEM is removed and the attached cells are fed with MEM supplemented with varying concentrations of day one colostrum, day eight milk and calf serum. Each medium is changed every third day, and after 12 days the cells are trypsinized and counted in a Coulter counter. Two and a half percent colostrum (by volume), the concentration producing the greatest effect, produces approximately the same cell count after 12 days as 5 percent serum.

Figure 5:
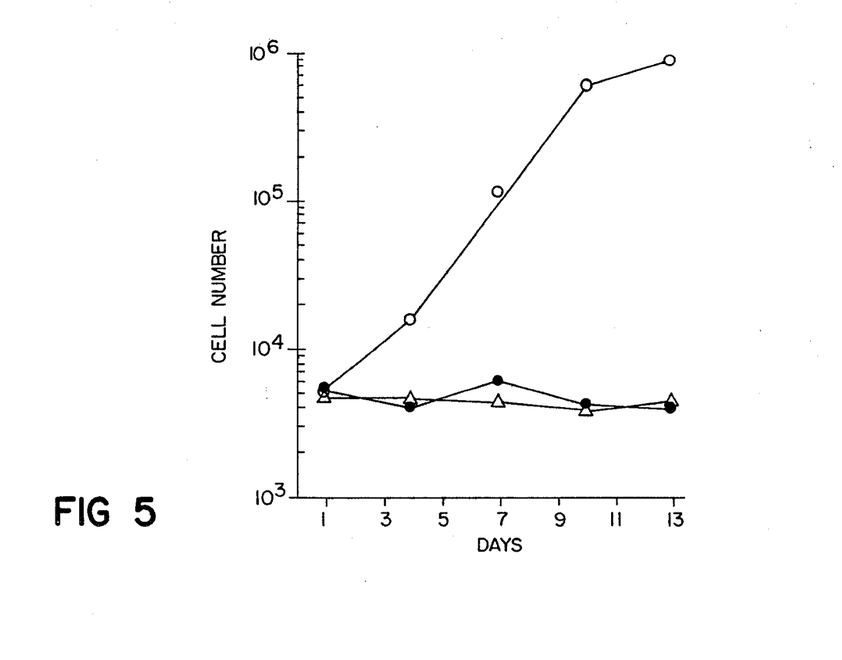
FIG. 5 is a graph of numbers of MDCK cells counted against time in days for: 2.5% (by volume) day 1 colostrum (o); 2.5% (by volume) day 8 milk (.); and unsupplemented medium ($\Delta$).

There is shown in FIG. 5 a time course curve of MDCK cell proliferation in day one colostrum, day eight milk and unsupplemented medium. MDCK cells in DMEM are seeded sparsely ($10^4$ cells/well, $5\times10^3$ cells/cm$^2$) into 24-well microliter plates. Six hours after plating the DMEM is removed and cells are fed with DMEM supplemented with 2.5 percent (v/v) day one colostrum, DMEM supplemented with 2.5 percent (v/v) day eight milk, and unsupplemented DMEM. Every third day cells in duplicate are counted and the remaining cells refed with fresh medium. After thirteen days the cell count for cells grown in 2.5 percent colostrum increases by a factor of between $10^2$ and $10^3$, while practically no proliferation is observed for cells grown in the other two media.

Table I below shows the number of MDCK cells counted after 9 days of feeding cells with colostrum in varying concentrations; cell numbers obtained with milk are also shown for purposes of comparison. MDCK cells are plated sparsely ($10^4$ cells per well, $5\times10^3$ cell/cm$^2$) into 24-well microliter plates. Three hours after plating, the DMEM is removed and attached cells are then fed every third day. It can be seen that colostrum very effectively promotes cell proliferation, and that 2.5% colostrum is more effective than 1.25% colostrum. Useful colostrum concentrations will vary, depending on the cell type cultured, but will ordinarily range between 0.5% and 20% of the medium, v/v.

TABLE I

| Proportion of Milk or Colostrum (% (v/v) in DMEM) | Final Cell Number |
|---|---|
| Day 1 colostrum (1.25%) | 360,000 |
| Day 8 milk (1.25%) | 3,800 |
| Day 1 colostrum (2.5%) | 440,000 |
| Day 8 milk (2.5%) | 4,200 |

Figure 6:
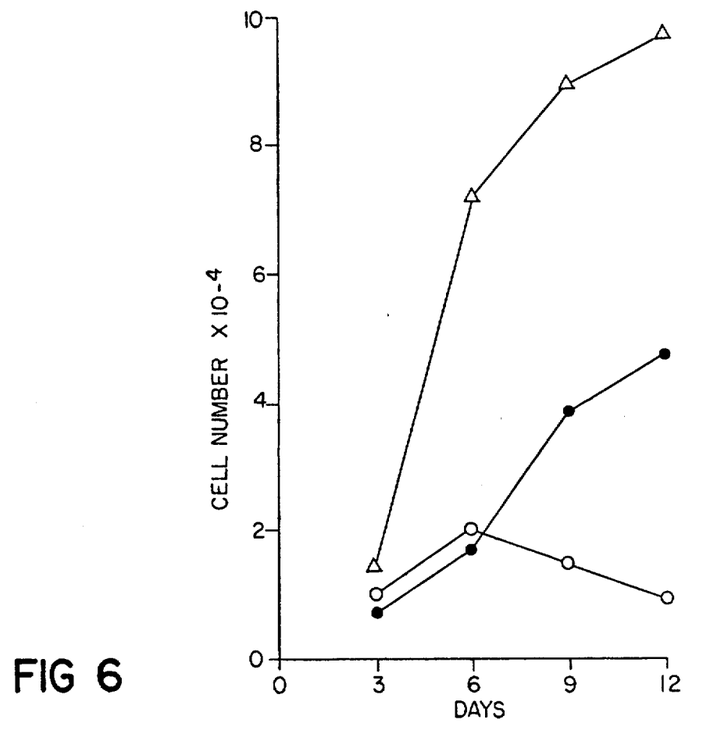
FIG. 6 is a graph of numbers of early passage fibroblasts counted against time in days for 2.5% (by volume) day 1 bovine colostrum (o); 2.5% (by volume) serum (.); and 2.5% (by volume) colostrum+2.5% (by volume) serum ($\Delta$).

There is shown in FIG. 6 a time course curve of early passage fibroblast proliferation in 2.5% day 1 bovine colostrum, 2.5% serum, and 2.5% bovine colostrum plus 2.5% serum all in DMEM. Plating and feeding procedure are as described for FIG. 5. FIG. 6 shows that, for unknown reasons, the fibroblasts proliferate at a higher rate in a colostrum-serum mixture than in either colostrum or serum alone. Thus colostrum and serum can be used together to provide a superior growth medium which is often cheaper than media containing serum alone. When serum and colostrum are used together, their concentrations will vary, depending on factors such as cell type and the desired growth rate. Useful serum concentrations will ordinarily range between 1 and 20% (v/v), and useful colostrum concentrations will ordinarily range between 0.2 and 5% (v/v).

Prevention of Fibroblast Overgrowth

Figure 7:
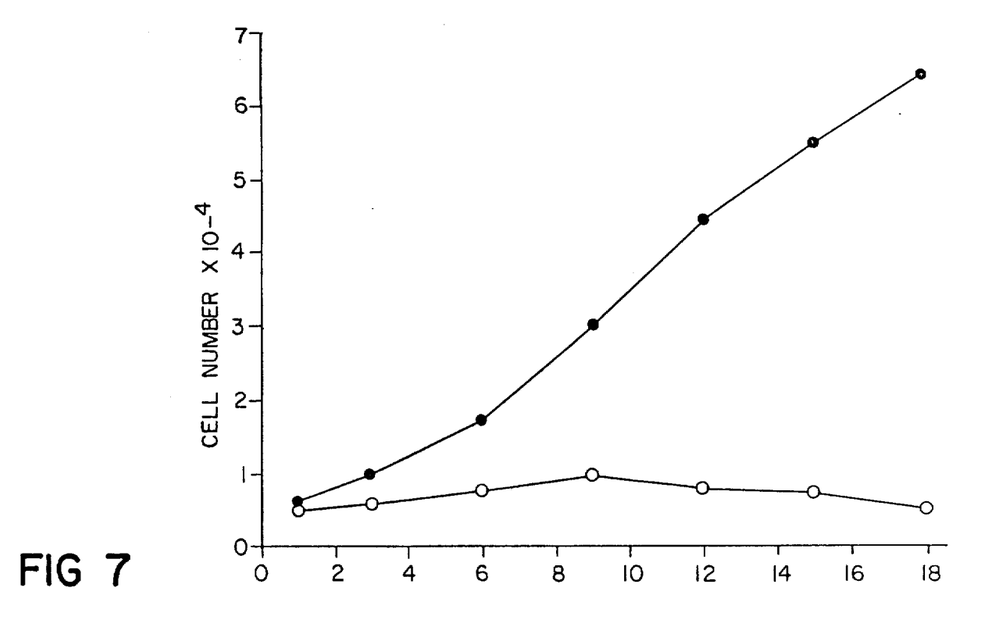
FIG. 7 is a graph of numbers of early passage fibroblasts counted against time in days for 2.5% (by volume) day 1 bovine colostrum (o) and 2.5% (by volume) serum (.).

There is shown in FIG. 7 a time course curve of early passage fibroblast proliferation in 2.5% (v/v) bovine colostrum (o) and 2.5% (v/v) serum (.), both in DMEM. Plating and feeding procedure are as described for FIG. 5. FIG. 7 shows that in colostrum, unlike in serum, early passage fibroblasts do not proliferate. This means that colostrum can be used in media to prevent fibroblast overgrowth, while still promoting the proliferation of a desired cell type, such as epithelial cells.

Media Containing Milk and Transferrin

Table II below shows the number of MDCK cells counted after 8 days of feeding cells with the media shown. All media are DMEM based. Human milk is obtained 4 months and bovine milk 6 days postpartum, except the last 2 data, which are for 3 month bovine milk. The ingredients other than milk, DMEM and serum are used in the following concentrations: Insulin, 5 µg/ml; EGF, 2.5 ng/ml; FGF, 50 ng/ml; Transferrin, 5 µg/ml. The culture method is the same as that described in relation to Table I above. Human and bovine milk in DMEM, in the absence of transferrin, fail to stimulate cell proliferation, as does transferrin, in the absence of milk. The proliferation-promoting activity of media containing both milk and transferrin approaches that of serum-containing media. Ten times as much 3 month milk must be used to obtain the proliferation rate of 6 day milk.

The amount of milk, transferrin, insulin, EGF, and FGF used will vary, depending on such factors as the age of the milk and the desired growth rate. Useful milk concentrations will ordinarily range between 1% and 25% (v/v). Transferrin concentration will ordinarily range between 1 and 25 µg/ml medium; insulin will range from 0 to 10 µg/ml medium; EGF will range from 0 to 10 ng/ml medium; and FGF will range from 0 to 100 ng/ml medium.

TABLE II

| Medium | Cell Number |
|---|---|
| 5% Human Milk, Insulin | 6,660 |
| 5% Human Milk, EGF | 7,500 |
| 5% Human Milk, FGF | 7,000 |
| 5% Human Milk, Insulin, EGF | 3,600 |
| 5% Human Milk, Insulin, FGF | 4,560 |
| 5% Human Milk, EGF, FGF | 2,700 |
| 5% Human Milk, Transferrin | 407,000 |
| 5% Human Milk, Transferrin, Insulin | 511,180 |
| 5% Human Milk, Transferrin, EGF | 513,360 |
| 5% Human Milk, Transferrin, FGF | 443,840 |
| 5% Human Milk, Transferrin, Insulin, EGF | 616,000 |
| 5% Human Milk, Transferrin, Insulin, FGF | 550,820 |
| DMEM, Transferrin, Insulin, EGF | 8,660 |
| DMEM | 6,000 |
| 1% Bovine Milk, | 3,260 |
| 1% Bovine Milk, Transferrin | 157,260 |
| 2.5% Bovine Milk, | 4,000 |
| 2.5% Bovine Milk, Transferrin | 95,000 |
| 5% Bovine Milk, | 7,220 |
| 5% Bovine Milk, Transferrin | 105,000 |
| 2.5% Bovine Colostrum, | 377,280 |
| 5% Bovine Serum, | 556,000 |
| 2% Bovine milk | 3,600 |
| 2% Bovine milk., insulin | 2,320 |
| 2% Bovine milk, EGF | 1,600 |
| 2% Bovine milk, FGF | 2,300 |
| 2% Bovine milk, insulin, EGF, FGF | 3,460 |
| 2% Bovine milk, insulin, EGF | 2,900 |
| 2% Bovine milk, insulin FGF | 4,400 |
| 2% Bovine milk, EGF, FGF | 3,960 |
| 2% Bovine milk, transferrin | 441,220 |
| 2% Bovine milk, transferrin, insulin | 563,420 |
| 2% Bovine milk, transferrin, EGF | 470,600 |
| 2% Bovine milk, transferrin, FGF | 500,720 |
| 2% Bovine,milk, transferrin, insulin EGF | 641,800 |
| 2% Bovine milk, transferrin, insulin FGF | 607,030 |
| 20% Bovine milk (3 month) | 6,760 |
| 20% Bovine milk (3 month), transferrin | 417,550 |

Colostrum-Based Media in Fibronectin-Coated Plates

Figure 8:
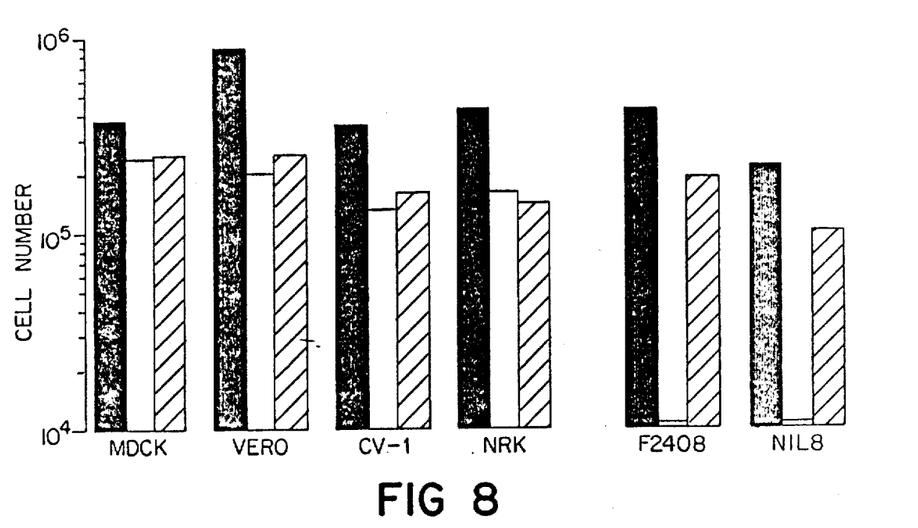
FIG. 8 is a bar graph showing relative numbers of six cell lines grown in serum, colostrum and colostrum plus fibronectin.

There is shown in FIG. 8 relative numbers of six of the cell lines, listed in Table IV below, grown in three media: 10% calf serum in DMEM (solid bars); colostrum (between 0.5 and 20%, depending on cell type) in DMEM in untreated dishes (open bars); and colostrum (0.5–20%) in DMEM in fibronectin-treated dishes (hatched bars).

Prior to exposure to test media, all cell types were detached from culture dishes by incubation with 1 ml of 0.25% trypsin and 0.2% EDTA in distilled water. An equal volume of soybean trypsin exhibitor (Type 1-S, Sigma, 0.25% in phosphate-buffered saline) was then added to stop the reaction. Cells were diluted in unsupplemented DMEM and then plated onto untreated or fibronectin-treated 24-well microliter plates (16 mm diameter, Costar, Cambridge, MA). Approximately three hours after plating, the supernatants were removed and the cultures then fed every 3–4 days by removing the culture supernatants and adding 0.5 ml of the appropriate medium.

To coat plates with fibronectin, human plasma fibronectin (Collaborative Research, Inc., Waltham, MA) was suspended in DMEM (25 μg/ml) and 0.4 ml were added to each well of the plate to attain a final fibronectin concentration of 5 μg/cm$^2$. The plates were incubated at room temperature for at least 30 minutes, the supernatants aspirated, and the cell suspension added immediately.

FIG. 8 shows that four of the six cell lines grew well in colostrum in untreated plates, while the two fibroblast lines grew in colostrum only when the plates had been pretreated with plasma fibronectin. The last two graphs of FIG. 8 show that fibronectin allowed the fibroblast cells to achieve a cell density which was 44% of that attained in serum. The colostrum concentration yielding maximal growth for each cell line (in treated and untreated plates) was: Vero, CV-1, and F2408, about 2% colostrum; MDCK, 2.5% colostrum, NRK, about 5% colostrum; NIL8, 2% colostrum with insulin (10 μg/ml) and transferrin (10 μg/ml). Useful colostrum concentrations for use with fibronectin will ordinarily range from 0.5% to 25%, v/v. Besides insulin and transferrin, EGF or FGF can also be added. Useful concentration ranges are: transferrin, 1 to 25 μg/ml medium preferably approximately 10 μg/ml; insulin, 0 to 10 μg/ml preferably approximately 10 μg/ml; EFG, 0 to 10 ng/ml; FGF, 0 to 100 ng/ml.

TABLE III

| | Cell Lines and Strains | | |
|---|---|---|---|
| Cell Type | Description | Source | Reference |
| MDCK | Madin-Darby canine kidney epithelial | Flow Laboratories Rockville, MD | Leighton et al. (1969) Science 163, 472 |
| CV-1 | African green monkey kidney epithelial | Dr. C. Scher, Sidney Farber Cancer Center, Boston, MA | Jensen et al. (1964) P.N.A.S. U.S.A. 52, 53 |
| Vero | African green monkey kidney cells | Dr. C. Scher. | Simizu et al. (1967) Proc. Soc. Exp. Med. 125, 119 |
| NRK | Normal rat kidney Cells | Dr. C. Scher | Duc-Nguyen et al. (1966) J. Bacteriol. 92, 1133 |
| F2408 | Fischer rat embryo cell line | Dr. C. Basilico New York University School of Medicine New York, NY | Frieman et al. (1973) P.N.A.S. U.S.A. 70, 2415 |
| NIL8 | Cloned hamster embryo cell line | Dr. R. Hynes Mass. Institute of Technology, Cambridge, MA | Diamond et al. (1967) Int. J. Cancer 2, 143 |
| 3T3 | Balb/c 3T3, clone A31 | Dr. C. Scher | Todaro et al. (1963) J. Cell Biol. 17, 299 |
| LR1 | Lewis rat embryo cells, Passage 2 | Dr. M. Klagsbrun | Steimer et al. (1977) J. Virol. 23, 133 |
| FS4 | Human foreskin fibroblasts, Passage 20 | Dr. D. Giard Mass. Institute of Technology, Cambridge, MA | None |
| Smooth muscle cells (SMC) | Bovine aortic Smooth muscle cells, Passage 7 | Dr. B. Zetter, Children's Hospital Medical Center, Boston, MA | Prepared by a modification of the method of Ross (1971) J. Cell Biol. 50, 172 |
| Chondocytes (BC) | Bovine articular cartilage chondrocytes, Passage 2 | Dr. M. Klagsbrun | Klagsbrun (1979) in Methods in Enzymology LVIII, Jakoby et al. eds., pp. 560–564 |

Milk-Based Media in Fibronectin-Coated Plates

Figure 9:
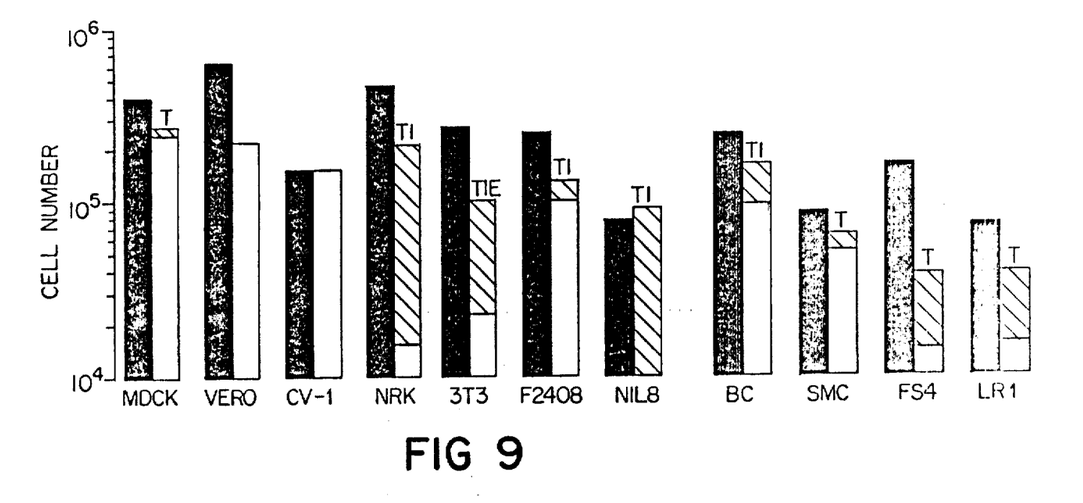
FIG. 9 is a bar graph showing relative numbers of eleven cell lines grown in serum, milk plus fibronectin, and milk plus fibronectin plus additives.

There is shown in FIG. 9 relative numbers of the cell lines listed in Table IV, above, grown in three media: 10% calf serum (solid bars); 10% day-80 milk plus fibronectin (open bars); 10% day-80 milk plus fibronectin plus one or more additives (hatched bars; T=transferrin, I=insulin, E=epidermal growth factor). Cell cultures and plates were prepared as described above for FIG. 8.

FIG. 9 shows that all 11 cell lines tested grew well in milk-based media in fibronectin-coated dishes, although some of the lines required additional factors to attain maximal growth, and one line, N1L8, did not grow at all in the absence of transferrin and insulin.

Milk concentrations will vary, depending on cell type cultured, and on the presence of additives. Useful concentrations will ordinarily range from 0.5% to 25% of the medium v/v preferably about 10%. FGF can also be added to the medium. Useful concentration ranges for additives are: transferrin, 1 to 25 µg/ml medium; insulin, 0 to 10 µg/l; EGF, 0 to 10 ng/ml; FGF, 0 to 100 ng/ml.

Measuring Malignant Cells

Table IV below shows cell counts after 10 days of feeding normal and 3 types of abnormal rat cell types with media containing 3 month bovine milk, bovine colostrum and bovine serum. Cells are plated in DMEM ($30 \times 10^3$ cells/well), 35° C., and after 2 hours DMEM is replaced with the desired medium. Cells are grown for 12 days. The two transformed cell types are grossly abnormal malignant cells. The established cell line F2408 is a rat fibroblast line which has been in culture for several years. These cells are abnormal, but not to the point of being malignant; they are analogous to premalignant cells.

Table IV shows that the two malignant cell types proliferate in all three media, including milk, while normal fibroblast cells fail to proliferate in milk or colostrum. Thus, for a cell sample containing both an unknown concentration of malignant cells and cells which do not proliferate in colostrum, e.g., normal rat fibroblast cells, the rate of cell proliferation in milk or colostrum-containing media is directly proportional to malignant cell concentration. If the sample is suspected of containing normal cells, e.g., epithelial cells, which proliferate in colostrum, the method is carried out with milk, not colostrum.

Because the cell line cells proliferate in colostrum but not in milk, the method can be used, for cell types such as fibroblasts which do not proliferate in colostrum, to measure premalignant cells; the rate of cell proliferation in colostrum is directly proportional to the concentration of premalignant cells. After this step, the method can be repeated with milk to determine the ratio of premalignant cells to malignant cells; only the malignant cells grow in milk.

Concentrations of milk and colostrum used in the method will vary, depending on such factors as cell type and age of milk. Useful milk concentrations will ordinarily range between 1% and 25% (v/v), and useful colostrum concentrations will ordinarily range between 0.5% and 25% (v/v).

tency can be used whenever milk and colostrum and employed. Fibronectin can be provided in the milk-based media, as well as on the culture plates. The milk and colostrum-based media can contain fibroblast growth factor as well as the other optional additives. Also, colostrum, in addition to being useful in tissue culture, may be useful in humans, e.g., in treating ulcers, or in counteracting the side effects of chemotherapy. Although human plasma fibronectin is preferred, fibronectin from any source can be used. Similarly, milk and colostrum from any mammal can be used.

I claim:

1. A cell culture medium comprising mammalian milk and fibronectin.

2. The medium of claim 1, further comprising at least one of the additives transferrin, insulin, epidermal growth factor, and fibroblast growth factor.

3. The medium of claim 1 wherein
said milk is bovine milk, and
said fibronectin is human plasma fibronectin.

4. The cell culture medium of any one of claims 1, 2, or 3, wherein said mammalian milk comprises, by volume, between about 0.5% and 25% of said medium.

5. The medium of claim 4 wherein said mammalian milk comprises, by volume, about 10% of said medium.

6. A cell culture medium comprising colostrum and fibronectin.

7. The medium of claim 6, further comprising at least one of the additives transferrin, insulin, epidermal growth factor, and fibroblast growth factor.

8. The medium of claim 6 wherein said colostrum is bovine colostrum, and said fibronectin is human plasma fibronectin.

9. The medium of any one of claims 6, 7, or 8, wherein said colostrum comprises, by volume, between 0.5% and 25% of said medium.

10. The medium of claim 9 wherein said colostrum comprises, by volume, between 2% and 5% of said medium.

11. The medium of claim 10 wherein said colostrum comprises, by volume, about 5% of said medium.

12. The medium of claim 10 wherein said colostrum comprises, by volume, about 2% of said medium.

13. The medium of claim 12 wherein said medium contains insulin and transferrin.

14. The medium of claim 13 wherein said insulin and transferrin are each present in said medium in the ap-

TABLE IV

| MEDIUM | NORMAL RAT FIBROBLASTS | ESTABLISHED RAT CELLS (F2408) | RSV TRANSFORMED RAT CELLS | TEMPERATURE-SENSITIVE RSV TRANSFORMED RAT CELLS (35°) |
|---|---|---|---|---|
| DMEM | 3,600 | 8,000 | 6,000 | 3,200 |
| DMEM + 10% Calf SERUM | 100,000 | 830,000 | 1,400,000 | 1,500,000 |
| DMEM + 10% Bovine Colostrum | 3,200 | 50,000 | 500,000 | 520,000 |
| DMEM + 10% Bovine Milk | 1,600 | 7,000 | 140,000 | 160,000 |

Other Embodiments

Other embodiments are within the following claims. For example, the growth-promoting concentrate purified from colostrum can be used in any of the aspects of the invention employing unpurified colostrum. Similarly, milk and colostrum which have been concentrated, powdered, previously frozen, or otherwise treated in a way which does not extinguish their poproximate concentration of 10 µg/ml.

15. A cell culture means comprising nutrient medium comprising mammalian milk, and a cell culture surface which is precoated with fibronectin.

16. The cell culture means of claim 15 wherein
said milk is bovine milk, and
said fibronectin is human plasma fibronectin.

17. A cell culture means comprising nutrient medium comprising colostrum, and a cell culture surface which is pre-coated with fibronectin.

18. The cell culture means of claim 17 wherein said colostrum is bovine colostrum, and said fibronectin is human plasma fibronectin.

19. A process of culturing cells comprising providing a cell culture substrate which is coated with fibronectin, introducing said cells onto said substrate, and providing the proper conditions for growth, including feeding said cells with nutrient medium comprising mammalian milk.

20. The process of claim 19 wherein said mammalian milk comprises by volume, between 0.5% and 25% of said medium.

21. The process of claim 20 wherein said mammalian milk comprises, by volume, about 10% of said medium.

22. The process of any one of claims 19, 20, or 21 wherein said medium further comprises at least one of the additives transferrin, insulin, epidermal growth factor, and fibroblast growth factor.

23. A process of culturing cells comprising providing a cell culture substrate which is coated with fibronectin, introducing said cells onto said substrate, and providing the proper conditions for growth, including feeding said cells with nutrient medium comprising colostrum.

24. The process of claim 23 wherein said colostrum comprises, by volume, between 0.5% and 20% of said medium.

25. The process of claim 24 wherein said colostrum comprises, by volume, about 2% of said medium.

26. The process of claim 24 wherein said colostrum comprises, by volume, about 5% of said medium.

27. The process of any one of claims 23, 24, 25, or 26 wherein said medium further comprises at least one of the additives transferrin, insulin, epidermal growth factor, and fibroblast growth factor.

28. A method of promoting proliferation of transformed or cancerous cells, said method comprising feeding said cells medium containing colostrum or mammalian milk.

29. The method of claim 28 wherein said medium comprises colostrum in an amount between 0.5% and 25% (by volume).

30. The method of claim 28 wherein said medium comprises mammalian milk in an amount between 1% and 25% (by volume).

31. A transformed or cancerous cell-proliferation medium comprising colostrum or mammalian milk.

32. The medium of claim 31 wherein said medium comprises between 0.5% and 25% (by volume) colostrum.

33. The medium of claim 31 wherein said medium comprises between 1.0% and 25% (by volume) mammalian milk.

* * * * *

UNITED STATES PATENT AND TRADEMARK OFFICE
CERTIFICATE OF CORRECTION

PATENT NO. : 4,440,860

DATED : April 3, 1984

INVENTOR(S) : Michael Klagsbrun

It is certified that error appears in the above-identified patent and that said Letters Patent are hereby corrected ~~as shown below~~: by adding the two attached sheets of drawings containing Figs. 6, 7, 8, and 9.

Signed and Sealed this

First Day of October 1985

[SEAL]

Attest:

Attesting Officer

DONALD J. QUIGG

Commissioner of Patents and Trademarks—Designate